United States Patent [19]

Abrahams

[11] 4,027,983

[45] June 7, 1977

[54] NOVEL GASKET AND FLOW CELL COMPRISING SAME

[75] Inventor: Louis Abrahams, Worcester, Mass.

[73] Assignee: Waters Associates, Incorporated, Milford, Mass.

[22] Filed: Apr. 9, 1975

[21] Appl. No.: 566,182

Related U.S. Application Data

[63] Continuation-in-part of Ser. No. 415,784, Nov. 14, 1973, Pat. No. 3,918,495.

[52] U.S. Cl. .............................. 356/246; 250/373; 356/181
[51] Int. Cl.² ...................... G01N 1/10; G01J 1/42
[58] Field of Search .................. 277/235 B, 235 A; 250/373; 356/246, 181

[56] References Cited

UNITED STATES PATENTS

| | | | |
|---|---|---|---|
| 2,812,777 | 11/1957 | Dahl | 92/102 |
| 3,567,234 | 3/1971 | Skrycki | 277/235 B |
| 3,866,926 | 2/1975 | Traum | 277/235 B |

Primary Examiner—Robert I. Smith
Attorney, Agent, or Firm—Robert A. Cesari; John F. McKenna; Andrew F. Kehoe

[57] ABSTRACT

A plate-like structure comprising a liquid flow path formed in one face thereof, a thin ductile seal-forming coating on the face of the structure which forms the flow path. The structure finds many utilities, most advantageously in constructing a novel valve wherein the disk is flexible and adapted for flexing a central face portion thereof against a conduit, thereby sealing said conduit.

8 Claims, 6 Drawing Figures

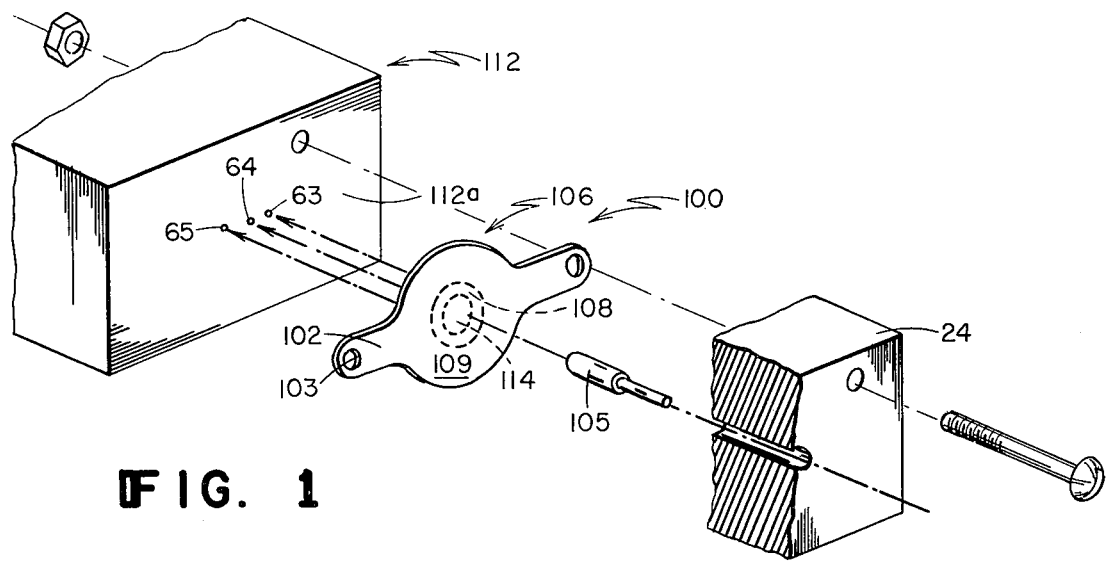
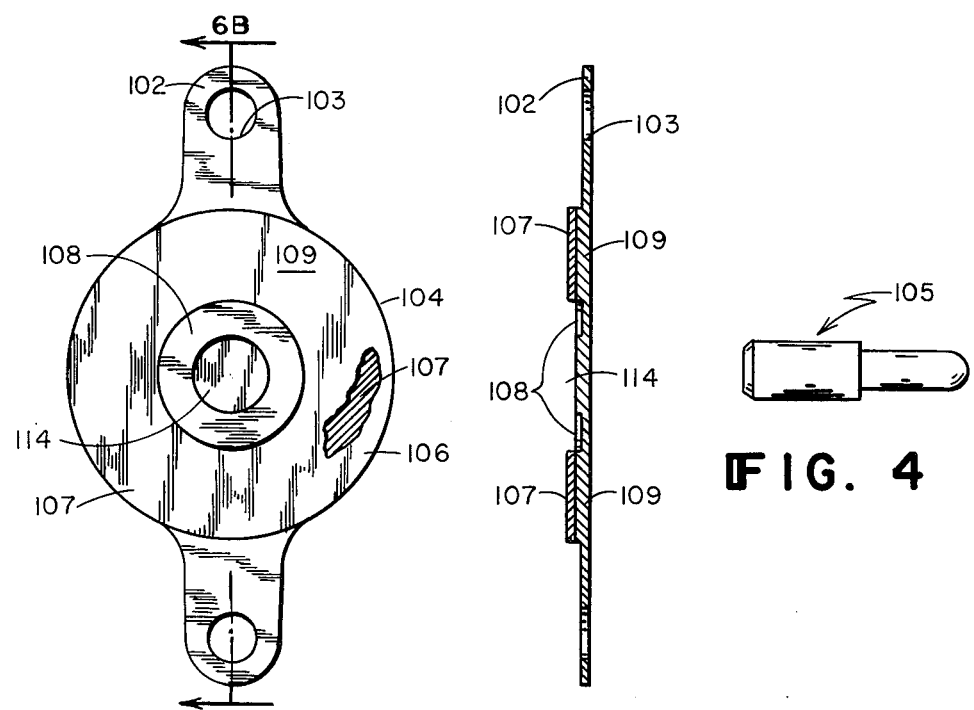

NOVEL GASKET AND FLOW CELL COMPRISING SAME

RELATED APPLICATION

This application is a continuation-in-part of U.S. Ser. No. 415,784 filed Nov. 14, 1973 by Abrahams and now U.S. Pat. No. 3,918,495.

BACKGROUND OF THE INVENTION

There have long been a number of problems encountered in achieving optimum flow patterns for small quantities of liquids being conducted through flow paths associated with analytical apparatus such as, for example, optically-sensitive apparatus like refractometers, ultraviolet absorbtion apparatus, etc. Such problems are also encountered in very small valves which are used with liquid analytical apparatus, e.g. liquid chromatography systems.

In general all of these problems relate to obtaining dependable displacement of the small quantity of liquid — often injected into a liquid carrier in microliter or submicroliter quantities — without undue dilution caused by excessively turbulent flow patterns and without undue contamination resulting from a previously utilized liquid or from leaching elastomeric seals. And, of course, the suitability of the apparatus for use at high pressures without leaking is generally a prerequisite for such flow paths.

Attempts to provide valves having desired reliability have included the use of relatively rigid plastic materials. (By "relatively rigid" is meant rigid as opposed to elastomeric synthetic polymers of the type used in gaskets at normal pressures.) These rigid materials have been used in making seats or other seal structure for valves used in injector mechanisms. Problems arise in use of such materials, they tend to absorb (and desorb) some of the broad spectrum of chemical compounds, with which they can be expected to contact. This feature not only tends to change their dimensions but also tends to provide a source for contaminants. Some tend to cold flow at high pressures. This becomes a major problem, even with such relatively creep-resistant materials as the polyacetal-type, whenever an attempt is made to incorporate them in tiny valves meant to moderate the flow of batch samples in the microliter range.

The thrust of innovation by others in this area appears to be development of small volume valves that really serve as sample holding devices e.g. slide valve as described in U.S. Pat. No. 3,748,833 to Karas et al, and can be pivoted or pushed from a sample-receiving position to a sample-flushing position. These devices are not particularly advantageous. Many depend upon elastomers for sealing limits; such dependence interferes with the structural stability of the valves because of cold flow and wear.

SUMMARY OF THE INVENTION

Therefore it is an object of the invention to provide an article, for use in forming low volume conduit-defining paths for low volume applications, wherein the article comprises both a flow-defining means and seal means.

Another object of the invention is to provide a flow-defining and seal means which is readily flushible.

Other objects of the invention will be obvious to those skilled in the art on reading the present invention.

The above objects have been substantially achieved by construction of an article primarily suited for use under compression and which comprises a think disk having a flow path formed in at least one face thereof, coated with a ductile sealant of less than about 0.002 inch in thickness, this sealant being at least on that side of the disk which comprises the flow path.

The disk itself is preferably not over about 0.030 inch in thickness and has an average diameter, or width if it be other than circular, of at least about twenty times the thickness of the metal. This permits compressive stresses applied thereto, to provide some flexibility and thereby facilitate the conformance of the sealant to the surface with which it is to be placed in sealing relationship. Of course, when the disk is used as a diaphragm in a valve the disk must be flexible enough to respond to valve operating means.

The ductile sealant advantageously is formed of synthetic polymeric materials such a polyvinyl chloride, polyethylene and the like. Polyhalocarbons such as polytetrafluoroethylene are the most advantageous materials because they strike an excellent balance between cost, chemical stability such as exemplified by resistance to contaminating fluids with leachable components, and ductibility. It is advantageous to have the polymeric coating about 0.001 inch in thickness, thus while it has the ability to exist as a freestanding film, it has no inherent three-dimensional shape, depending on its adherence to the underlying disk to assume its ring-like stucture exhibited in the article of the invention.

The disk itself is preferably formed of stainless steel or some other flexible but non-ductile metal.

The flow path formed in the disk, and taking the sealant coating into account, is desirably no greater than about 0.010 inch in depth for small valve applications, but can be as deep as 0.030 inch in some advantageous gasket configurations and conveniently can be as low as 0.002 inch in depth. Preferably the depth of the flow path is equal to at least twice the thickness of the sealant coat. In apparatus associated with analytical devices such as liquid chromatographs, refractometers, U.V. absorbing devices and the like, the volume of the flow path is advantageously below 0.001 cubic centimeter.

ILLUSTRATIVE EXAMPLE OF THE INVENTION

In this application and accompanying drawings there is shown and described a preferred embodiment of the invention and suggest various alternatives and modifications thereof, but it is to be understood that these are not intended to be exhaustive and that other changes and modifications can be made within the scope of the invention. These suggestions are selected and included for purposes of illustration in order that others skilled in the art will more fully understand the invention and the principles thereof and will be able to modify it in a variety of forms, each as may be best suited in the condition of a particular case.

IN THE DRAWINGS:

FIG. 1 is a perspective and exploded view of a novel valve utilizing the flow-defining article of the invention.

FIG. 2 is a plan view of the flow-defining disk.

FIG. 3 is a section through said gasket article.

FIG. 4 is a view of the valve operating rod.

Figure 5:
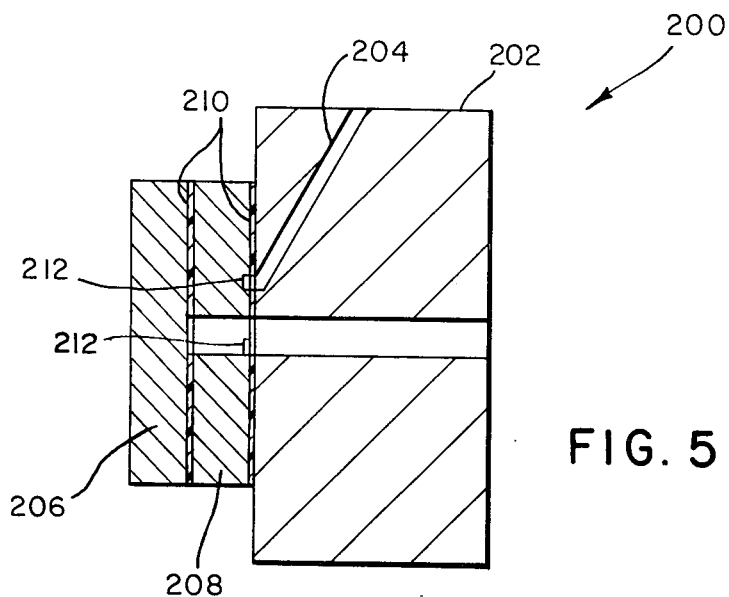
FIG. 5 is a schematic section of a flow cell using a flowpath defining gasket of the invention.

Before describing the valve in detail, the following list of advantageous features is set forth:

a. The valve has substantially no excess volume not serving to augment the flow capacity thereof.
b. The valve has no conventional elastomeric structural members; but it does have a thin, less than about 0.002 inches and advantageously about 0.001 inches thick, coating of a polymeric coating like a polytetrafluorethylene is advantageous because of its chemical inertness; it also has exceptional resistance to excessive feathering at high pressures.
c. There is substantially no deadspace in the valve; by "deadspace" is meant volume wherein liquid can be desposited and resist quick-removal by flushing of the valve. The illustrated valve has no deadspace and only about 0.001 in $^3$ of volume to be flushed; even this volume can easily be reduced to small fraction of that if required.
d. The valve can be quickly and conveniently moved between open and shut positions by push-pull mechanism, thereby making it particularly well adapted to automatic control. This push-pull mechanism, thereby making it particularly well adapted to automatic control. This push-pull action is absolutely free of sliding contact between parts within the liquid-containing chamber of the valve.
e. There is little or no valve structure promoting mixing or disturbance of plug-flow of liquid therethrough.
f. The valve provides an effective means to allow the joinder of one fluid with an existing flow path. As such, it serves not only the function of a valve but a valved T-connection in a piping system.
g. The valve can be easily inspected and replaced.

FIGS. 1 through 3 illustrate a valve 100 comprising a generally flat, thin, metallic disk 106 with positioning ears 102 apertured at 103 to provide means to position the valve to structure of an assembly. The ears are slightly recessed in the illustrated embodiment: The main body 104 of the valve comprises operating disk 106 of stainless steel, a coating of corrosion-resistant, chemically inert, polymer 107 on the outer annular surface 109 thereof. Disk 106 has in its face a circular groove 108 adapted to form a flow path 110. The valve comprises, on a single face 112a of the housing inlet and outlet conduits necessary for its operation, e. g. 63, 64 and 65.

A valve operating rod 105 is centrally mounted with respect to disk 106 to flex it downwardly into contact with housing 112. When the disk is allowed to flex away from housing 112, liquid may flow into (or out of, as in the present apparatus) the valve structure from a centrally located port 64 which is blocked by central sealing surface 114, when the disk is flexed toward port 64.

The thin stainless steel disk comprises a polytetra-fluroethylene coating of about 0.001 inch thick as a sealing means. In fact this disk is at once a gasket and a diaphragm because the coating serves as a seal in high-pressure applications.

When the disk is in its closed position, i.e. with central sealing face 114 pressed against conduit 64 by operating rod 105, liquid can flow through the inlet port from conduit 65 halfway around surface 114, via the conduit formed by peripheral groove 108 and housing member 112a, and the port to conduit 63 which serves as the outlet port of the valve. However, when the disk is allowed to resume its normal and non-flexed position, face 114 is retracted from contact with the port to conduit 64 and liquid entering the valve through port 65 is free to flow through the port to conduit 64 as well as the port to conduit 63.

Figure 6:
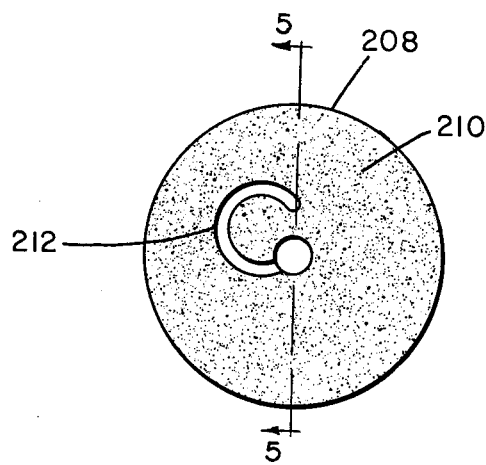
FIG. 6 is a view of the face of the gasket shown in FIG. 5.

Another application for the article of the invention which comprises both flow-path and gasket utility is used in the manufacture of a flow cell 200 as seen in FIGS. 5 and 6:

Flow cell 200 is of the general type used in ultra-violet light, absorption-measuring apparatus, in refractometers and other such devices. In all such flow cells there is a desirability to avoid any light refracting or light-reflecting phenomena along the optical path because of flow characteristics. Moreover, it is desirable to bring sample flow in from the bottom of such cells to avoid any possible gas entrapment near an elevated entrance port. Finally, it is desirable to be able to build sample cells that can be tailored to any optimum configuration of sample flow path.

Referring to FIG. 5, there is seen a flow cell 200 having a housing 202 with an inlet flow path 204 therein. At the front of the cell is a window 206 and, forming a flow path between window 206 and housing 202, is a flow-path defining gasket 208 with an elastomeric seal coating 210 on each side thereof.

FIG. 6 indicates the coating 210 which is again but 0.001 inch of organic polymer like polytetrafluoroethylene. A flow path 212 has been etched into the disk which is about 0.012 inch thick and formed of stainless steel.

In general, this self-sealing, flow-path defining gasket comprising a feathering-resistant layer of less than about 0.002 inch of polymer as a seal is highly versatile in that its use makes the implementation of any flow path configuration relatively easy.

Thus, applicant has provided a flow cell wherein a gasket comprises an aperture adapted to form part of the optical path. Advantageously, the flow cell is formed of a thin metallic support structure having a channel on one face thereof and comprising a coating of less than 0.002 inch of an organic plastic material.

As indicated above, this coating is advantageously of a polyhalocarbon and, most desirably, of polytetrafluoroethylene. The volume of the channel is, as in the case with the valve described above, less than about 0.002 inches thick and contains a volume of less than 0.001 cc.

It will be noted that the disk member is held in compression between its adjacent members manifold block 112 and also member 24. These, in effect, form the valve housing. Means by which they are held in compression are known in the art; e.g. they can be a simple nuts-and-bolts arrangement. Such means are not shown in detail in the drawings because it is not believed that they, per se, add any novelty to the invention and therefor are not required illustration to explain the invention to any skilled in the art.

It will thus be seen that the objects set forth above, among those made apparent from the preceding description, are efficiently attained and, since certain changes may be made in carrying out the above method without departing from the scope of the invention, it is intended that all matter contained in the above description shall be interpreted as illustrative and not in a limiting sense.

What is claimed is:

1. In a flow cell apparatus of the type comprising a liquid flow path along an optical path, and an inlet to said flow path from the bottom thereof, the improvement wherein said inlet flow path includes a segment thereof formed in a gasket compressed between said flow cell housing member and a window member, said gasket comprising an aperture forming a portion of said optical path and also a portion of said liquid flow path, and said inlet flow path being formed as a channel in on one side of said gasket and terminating at the bottom of said aperture.

2. A flow cell as defined in claim 1 wherein said gasket consists essentially of a thin metal support structure having a channel forming said inlet flow path in one face thereof and comprising a coating, of up to about 0.002 inch thickness, of a polyhalocarbon.

3. A flow cell as defined in claim 2 wherein said coating is formed of a polytetrafluoroethylene.

4. A flow cell as defined in claim 2 wherein said substrate is a flexible metallic substrate.

5. A flow cell as defined in claim 1 wherein said coating is less than about 0.002 inch thick.

6. A flow cell is defined in claim 5 wherein the volume of said channel is less than 0.001 cc.

7. A flow cell as defined in claim 1 wherein the volume of said channel is less than 0.001 cc.

8. A flow cell as defined in claim 1 wherein said substrate is a flexible metallic substrate.

* * * * *